(12) United States Patent
Bello et al.

(10) Patent No.: US 8,907,909 B2
(45) Date of Patent: Dec. 9, 2014

(54) DYNAMIC MODULAR CONTROL SYSTEM

(75) Inventors: Musodiq O. Bello, Greenfield, WI (US); Gopal Biligeri Avinash, Menomonee Falls, WI (US); John David Hoford, Pewaukee, WI (US); Aparna Nittala, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 13/482,566

(22) Filed: May 29, 2012

(65) Prior Publication Data

US 2013/0321284 A1    Dec. 5, 2013

(51) Int. Cl.
*G06F 3/041*    (2006.01)

(52) U.S. Cl.
USPC .......................................................... 345/173

(58) Field of Classification Search
CPC ............ G06F 3/041; G06F 3/00; G06F 3/048
USPC .......................................... 345/170–176, 1.1
See application file for complete search history.

(56) References Cited

U.S. PATENT DOCUMENTS

| | | | |
|---|---|---|---|
| 7,263,710 B1 | 8/2007 | Lamoureux et al. | |
| 7,301,451 B2 | 11/2007 | Hastings | |
| 7,483,939 B2 | 1/2009 | Mussack | |
| 7,606,720 B1 | 10/2009 | Kerpelman et al. | |
| 2004/0032393 A1* | 2/2004 | Brandenberg et al. | 345/156 |
| 2005/0152589 A1* | 7/2005 | Wehnes et al. | 382/128 |
| 2008/0029707 A1 | 2/2008 | Kari et al. | |
| 2008/0256181 A1 | 10/2008 | Morita et al. | |
| 2011/0010087 A1* | 1/2011 | Wons et al. | 701/201 |
| 2011/0015858 A1* | 1/2011 | Takagi et al. | 701/201 |
| 2011/0029913 A1* | 2/2011 | Boillot et al. | 715/776 |

* cited by examiner

*Primary Examiner* — Andrew Sasinowski
(74) *Attorney, Agent, or Firm* — Dean D. Small; The Small Patent Law Group

(57) ABSTRACT

A modular control system including a plurality of individual touch screen devices, each touch screen device including a display unit, a touch input, a computing device, a network connection, and a programming logic for controlling a remote system and displaying a status of the remote system on the touch screen device, the remote system having network connectivity to enable the remote system to exchange information with and respond to instructions from the touch screen devices, the touch screen devices configured for automatic self-synchronization based on a status of the remote system or a status of at least one of the touch screen devices.

14 Claims, 5 Drawing Sheets

DYNAMIC MODULAR CONTROL SYSTEM

BACKGROUND OF THE INVENTION

The subject matter disclosed herein relates generally to control systems, and more particularly to a dynamic modular control system for controlling an imaging system.

Control room design plays a major role in acquiring, processing, managing and efficiently presenting data, as well as controlling industrial and other devices. Control rooms are used in various applications such as healthcare applications, military applications, emergency services, the security industry, as well as the utilities, transportation, satellite systems, nuclear power plants, to name just a few applications.

The design and layout of control rooms has changed over the years to achieve a broader spectrum of functionality and efficiency. The complexity of control room designs may vary from a simple layout of two plugged monitors to a highly complex set of multiple integrated systems. In operation, the control room is utilized to monitor and control the operation of a remote system. More specifically, the control room may include a centralized computer that is hardwired to remote control devices which are typically installed near the remote system. The local control devices are typically implemented as switches or buttons that are permanently mounted in close proximity to the system being controlled. Moreover the local control devices typically perform only a single function, such as for example, raising or lowering a medical imaging system table. While the centralized computer is configured to perform control functions on the system, the centralized computer typically does not perform all the control functions. For example, the centralized computer may not be able to control the functions of one or more of the local control devices. Accordingly, the centralized computer located in the control room does not provide a redundancy to operate the system in the event that the local control device becomes inoperative.

SUMMARY OF THE INVENTION

In one embodiment, a modular control system is provided. The modular control system includes a plurality of individual touch screen devices, each touch screen device including a display unit, a touch input, a computing device, a network connection, and a programming logic for controlling a remote system and displaying a status of the remote system on the touch screen device, the remote system having network connectivity to enable the remote system to exchange information with and respond to instructions from the touch screen devices, the touch screen devices configured for automatic self-synchronization based on a status of the remote system or a status of at least one of the touch screen devices.

In another embodiment, a modular control system is provided. The modular control system includes a system configured to communicate with a network, and a plurality of portable touch screen devices, each touch screen device including a display unit, a touch input, a computing device, a network connection, and programming logic for controlling the system, managing specific functions of the system and displaying the status of the system on the touch screen device via the network.

In a further embodiment, a portable touch screen device is provided. The portable touch screen device includes a housing, a communication module within the housing configured to wirelessly communicate with at least one medical device and at least one different portable touch screen device using a communication grid, and a display displaying a graphical user interface to control the at least one medical device, the portable touch screen device configured for automatic self-synchronization based on a status of at least one of the medical device or a status of a different portable touch screen device.

DETAILED DESCRIPTION OF THE INVENTION

Figure 1:
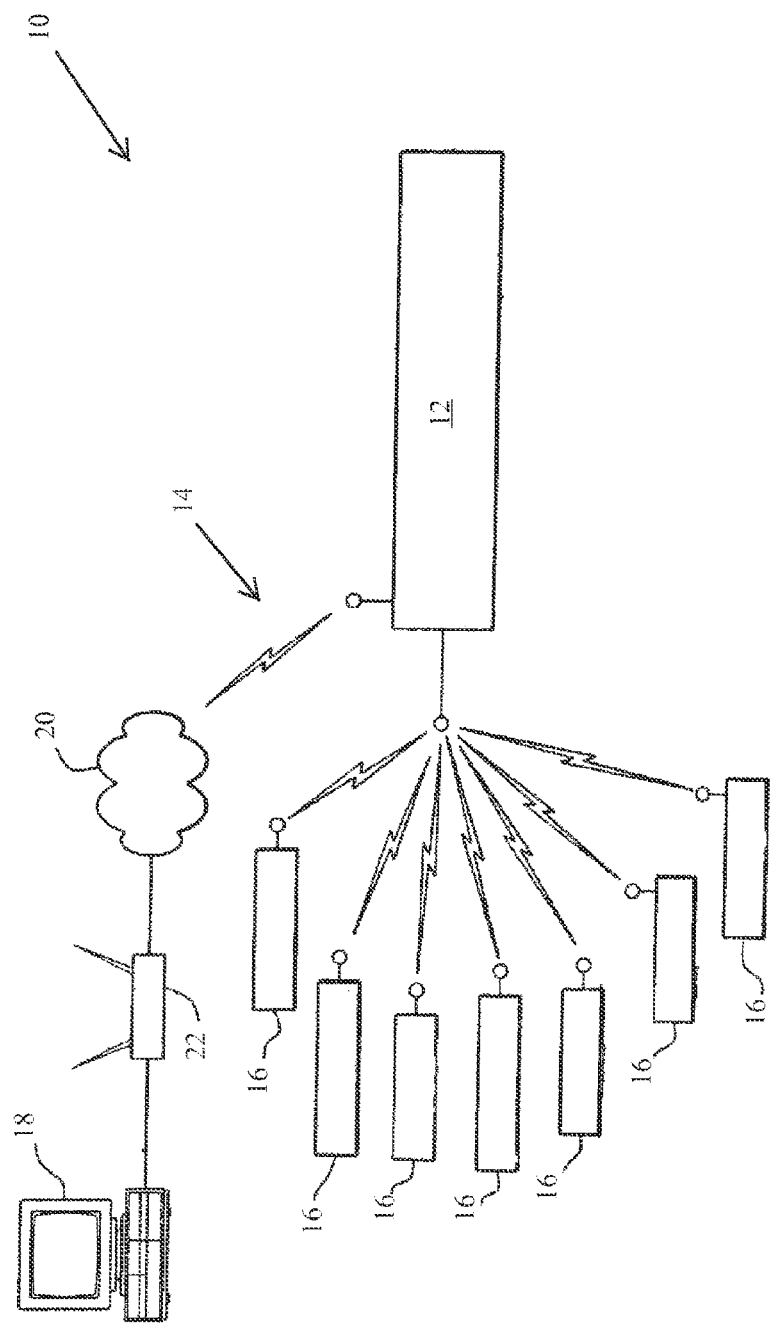
FIG. 1 is a schematic block diagram illustrating a control and monitoring system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, plurality may mean one or more devices as used herein.

As used herein the term "module" refers to software, hardware, for example, a processor, or a combination thereof that is programmed with instructions for performing an algorithm or method. The modules described herein may communicate wirelessly or through a wired connection.

Various embodiments provide a control and monitoring system for controlling and monitoring an integrated system, such as for example, a medical imaging system. The control and monitoring system generally includes a communication grid and a plurality of controllable devices communicatively coupled to the communication network or grid. The control and monitoring system also includes a plurality of user interfaces that are communicatively coupled to the communication network and configured for automatic self-synchronization based on a status of at least one of the controllable devices or a status of at least one of the user interfaces. In various embodiments, at least some of the user interfaces may be implemented as portable devices, such as an electronic tablet type device. In other embodiments, at least some of the user interfaces may be any portable or handheld device. Portable devices include any device is easily transportable from one location to another location. In other embodiments, portable devices include devices that are hand carried. Thus, while some of the portable devices may be temporarily stored in a bin or holder to enable the operator to conveniently utilize the portable device, the portable devices may be easily removed from the bin or holder and hand carried to another different location. In various embodiments, the tablet type device may be a touch-screen type of computing device. By practicing at least one embodiment, a more robust control and monitoring system may be provided that increases system redundancy.

FIG. 1 is a schematic block diagram illustrating a control and monitoring system 10 for controlling and monitoring an integrated system. In the illustrated embodiment, the integrated system is a medical system 12. The medical system 12 may be any type of medical system. In some embodiments, the medical system 12 is a patient care or patient monitoring device. For example, the medical system 12 may be monitors, such as blood rate monitors or blood pressure monitors, a ventilator, or an electrocardiogram, among other devices. It should be noted that some of the medical systems may be standalone devices or integrated into a single system. In various other embodiments, the medical system 12 may be a medical imaging system. Such medical imaging systems, include for example, a Positron Emission Tomography (PET) system, a Single Photon Emission Computed Tomography (SPECT) system, a Magnetic Resonance Imaging (MRI) system, a computed tomography (CT) imaging system, an ultrasound imaging system, and/or an X-ray system, among others.

The control and monitoring system 10 also includes a communication network 14 and a plurality of portable user interfaces 16. In operation, the user interfaces 16 are configured to communicate with the medical system 12 via the communication network 14. The control and monitoring system 10 may also optionally include a server 18. The server 18, may be a larger computing machine and include several separate modules, etc, and configured to communicate with the medical system 12 via the communication network 14.

In various embodiments, the communication network 14 may be implemented as a local area network (LAN). For example, the LAN may be implemented as a Wi-Fi network (IEEE 802.11) or Bluetooth network to enable the user interfaces 16 to communicate wirelessly with the medical system 12, the server 18, and other user interfaces 16. In other embodiments, a portion of the communication network 14 may be implemented using a wired connection, such as for example, by a wired IEEE 802.3 (Ethernet) connection and/or a universal service bus (USB) or FireWire (IEEE 1394) connection. For example, the server 18 may communicate with the medical system 12 via the Ethernet while the user interfaces 16 communicate with the medical system 12 via USB connections. Moreover, in some embodiments, the server 18 may communicate with the medical system 12 and the user interfaces 16 via the Internet 20. For example, the server 18 or a portion of the user interfaces 16 may be coupled to a router 22 that enables information to be transmitted to and/or from various devices in the control and monitoring system 10 via the Internet. While various embodiments are described with respect to a healthcare setting, the control and monitoring system 10 may be used in other non-healthcare settings.

Figure 2:
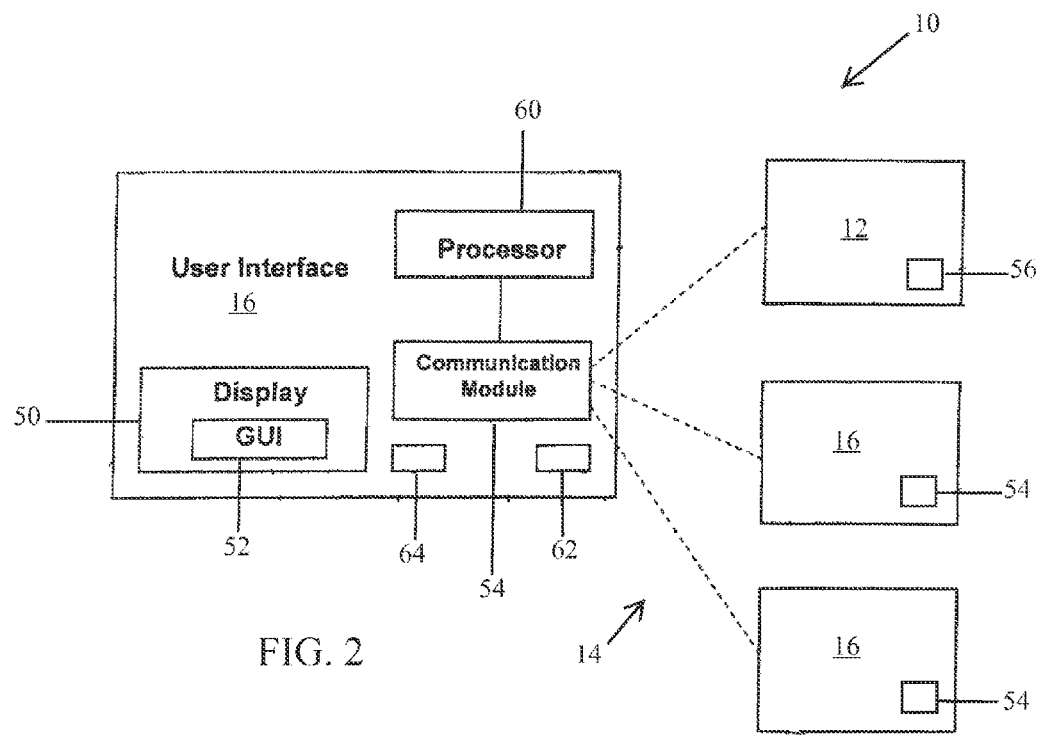
FIG. 2 is a simplified schematic block diagram of the user interface shown in FIG. 1 in accordance with various embodiments.

FIG. 2 is a simplified schematic block diagram of the user interface 16 shown in FIG. 1. As described above, the control and monitoring system 10 includes the communication network 14 and the user interfaces 16, which in various embodiments are implemented as electronic tablet devices or other portable or handheld electronic devices. For example, the user interface 16 in one embodiment is a tablet computer device or other mobile computer installed in a housing 48 (shown in FIG. 3). The user interface 16 also includes a display 50, such as integrated into a flat touch-screen and operable by touching the screen instead of using a physical keyboard. For example, the display 50 may display an onscreen virtual keyboard and also allows use of a passive stylus pen or a digital pen.

It should be noted that the user interface 16 may be embodied in different sizes and shapes, such as based on the particular application and the information to be displayed on the display 50. Thus, the user interface 16 encompasses different form factors and allows different information to be displayed on different portions of the display 50 that may include user selectable elements as described in more detail herein. In some embodiments, an integrated physical keyboard may be provided that rotates for storage when not in use.

The user interface 16 also provides a graphical user interface (GUI) 52 displayed on the display 50. In one embodiment, the user interface 16 includes preloaded applications of different GUIs 52 for communicating with and/or controlling one or more devices, such as for example, the medical system 12 and/or other user interfaces 16. It should be noted that although one system 12 is illustrated, the user interface 16 may be configured to communicate with additional systems. As described above, the system 12, in the illustrated embodiment, is a medical system.

The user interface 16 also includes a communication module 54 for communicating with the medical system 12, the optional server 18, and other user interfaces 16. For example, the medical system 12, in one embodiment, includes a communication module 56 that allows bi-directional communication between the medical system 12, the user interfaces 16, and the server 18. Moreover, the communication module 54 allows bi-directional communication between the medical system 12, the server 18, and other user interfaces 16. The communication modules 54 and 56 may include, for example, a transmitter and receiver arrangement for communicating there between. It should be noted that any suitable wireless communication technology may be used, such as a device to device communication method (e.g., Bluetooth, Infrared control, radio frequency control, etc.), such as to create a personal area network, or a broadcast type of communication method (e.g., Wi-Fi, network, etc.). In various embodiments, the communication scheme or method allows secure communication, such as within a room of a hospital.

The communication modules 54 and 56 may be configured so as to not interfere with the medical system 12. The communication modules 54 and 56 may also communicate using a digital protocol for transmitting information and commands between the user interfaces 16 and the medical system 12. The communication module 54 allows additional functionality, which may be provided in connection with a processor 60 (e.g., central processing unit) and a memory 62. For example, in one embodiment, the communication module 54 includes an application for detecting remote controllable devices (e.g., one or more medical devices associated with the medical system 12) in the vicinity of the user interface 16 (e.g., in the same room as the medical system 12). The user interface 16 also allows visualization of the medical system 12, such as by replicating or emulating a control interface of one or more of the control systems forming a part of the medical system 12 on the display 50 as part of the GUI 52.

Additional components may be provided as part of the user interface 16. For example, a local global positioning system (GPS) device 64 may be provided as part of the user interface 16. However, is should be noted that any suitable system or method (including Bluetooth, Wi-Fi, radio frequency, and infrared-based systems) for providing a location of the user interface 16 may be used and GPS is merely one example. In various embodiments, the memory 62 may store applications to control and monitor various devices associated with the medical system 12, as well as other information that is downloaded or uploaded to/from the medical system 12 or the server 18.

It also should be noted that the user interface 16 may be operated in the same location as the medical system 12, such as in the same room or in a different location than the medical system 12, such as outside the room where the medical system 12 is located, but within the same area.

In various embodiments, the user interface 16 allows remote control of the medical system 12 without having to physically touch the medical system 12. The user interface 16 also allows access to stored data within the medical system 12, such as to view or upload monitoring data. The display 50 may display any type of data or images. Thus, the user interface 16 may provide real-time control of the medical system 12.

It should be noted that the user interface 16 may also communicate with other devices using the communication module 54. For example, the user interface 16 may provide communication with peripheral devices, such as printers or scanners, e.g. document scanners. Additionally, the user interface 16 may communicate with a host system, such as a medical data system or the server 18 shown in FIG. 1, or with another system 12 so that multiple devices can be controlled in the same grid.

It should also be noted that the user interface 16 may be used for other operations. For example, patient information may be input, such as an observed state of the patient or information received from the patient (e.g., answers to medical questions). Other types of information also may be entered or updated, such as background information, such as patient address and insurance information, as well as, physical information, such as patient height, weight, age, allergies, medical history or the like. Information entered into the user interface 16 or accessed and uploaded from the medical system 12 may be electronically transmitted to the server 18 for long term storage.

Other information also may be tracked, such as a time of the patient visit, the conditions in the room (e.g., temperature, light level, etc.) or any other information that may be clinically relevant, such as for monitoring the patient and progression of any treatments. A picture of the patient may also be electronically captured using the built-in camera on the mobile device as described below.

Figure 3:
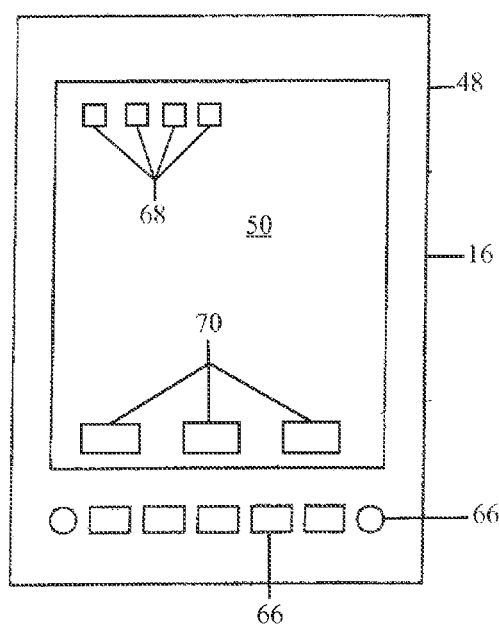
FIG. 3 illustrates the user interface shown in FIG. 2 in accordance with various embodiments.

FIG. 3 illustrates the user interface 16 as a portable handheld device. The user interface 16 provides remote control of the medical system 12 (shown in FIG. 1). For example, the user interface 16 is untethered from the medical system 12 and may be used remotely therefrom, inside or outside of the room having the medical system 12. For example, an operator may directly control various control functions of the medical system 12 or all of control functions of the medical system 12 while observing the patient. Thus, the user interface 16 communicates with the medical system 12 to control functions and operations of the medical system 12, which may include, for example, remotely changing settings of the medical system 12.

The user interface 16 includes the display 50 for displaying information, such as the GUI 52 (shown in FIG. 1). The display 50 has a resolution capable of displaying desired or required types of information. In one embodiment, the display 50 is a touch sensitive display that displays information and concurrently allows for one or more portions of the display 50 to be touch sensitive portions. For example, at least a portion of the display 50 is able to detect the location of an operator's touch on the display 50. Various types of touch technologies are available for use in touch sensitive displays, including but not limited to touch sensitive elements such as capacitive sensors, membrane switches, and infrared detectors. It also should be noted that the touch sensitive display may be different types of touch sensitive displays. For example, the touch sensitive display may be a single touch display or a multi-touch display. Thus, the display 50 in some embodiments may provide single touch capabilities or multi-touch capabilities (e.g., recognizing two or more points of contact, which may allow scrolling, pinch to zoom, etc, with multiple touches).

The user interface 16 optionally includes one or more input devices 66, such as buttons provided in a keypad that is separate from the display 50. Alternatively, the display 50 may be a touch-screen display having the input devices incorporated therein (e.g. virtual buttons). The user interface 16 may optionally include other components, for example, an audio device, such as a speaker, a camera, and/or a microphone.

The user interface 16 may also display icons 68 to select various applications or menus 70 for selecting various applications and/or controlling the medical system 12 as described in more detail below. The icon based applications 68 may have images to facilitate easier identification of associated functions, etc. In some embodiments, the GUI 52 is displayed having an appearance that emulates the appearance of the control interface of one or more controllers that form a portion of the medical system 12 as described in more detail below. It should be noted that the GUI 52 may emulate the display, virtual controls and/or physical controls of the medical system 12. The user interface may also dynamically change its interface based on its location with respect to the system being controlled.

Figure 4:
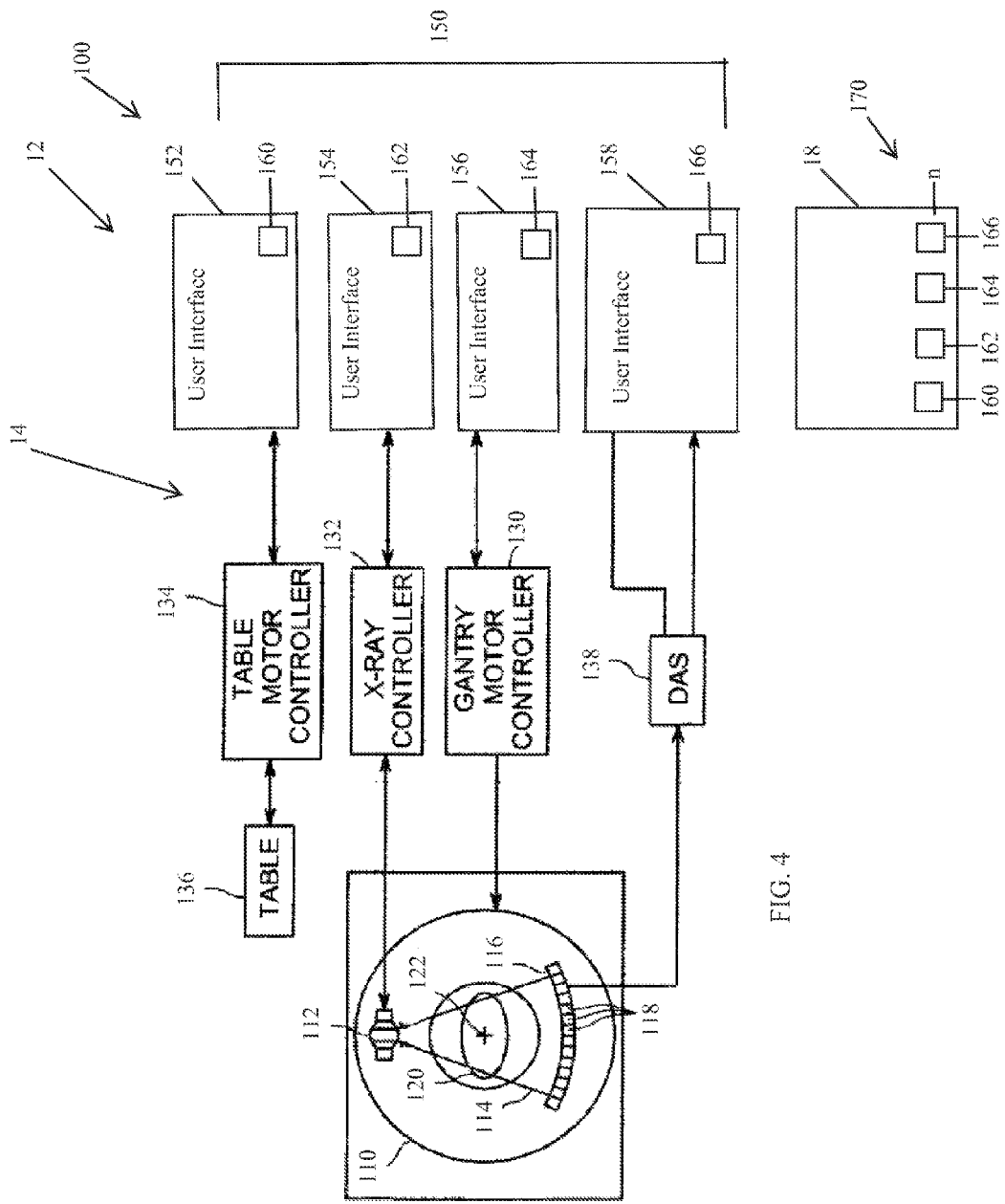
FIG. 4 is a block schematic diagram of an exemplary medical system formed in accordance with various embodiments.

FIG. 4 is a diagram of an exemplary medical system, such as the medical system 12 shown in FIG. 1. In the illustrated embodiment, the medical system 12 is a CT imaging system 100. However, as explained above, the medical system 12 may be implemented as a variety of imaging systems or medical diagnostic or monitoring systems. The CT imaging system 100 includes a gantry 110 that has an x-ray source 112 that projects a beam of x-rays 114 toward a detector array 116 on the opposite side of the gantry 110. The detector array 116 includes a plurality of detector elements 118 that are arranged in rows and channels that together sense the projected x-rays that pass through an object, such as a patient 120.

Each detector element 118 produces an electrical signal, or output, that represents the intensity of an impinging x-ray beam and hence allows estimation of the attenuation of the beam as it passes through the patient 120. During a scan to acquire x-ray projection data, the gantry 110 and the components mounted thereon rotate about a center of rotation 122. FIG. 4 shows only a single row of detector elements 118 (i.e., a detector row). However, the multislice detector array 116 includes a plurality of parallel detector rows of detector elements 118 such that projection data corresponding to a plurality of slices can be acquired concurrently during a scan.

Rotation of the gantry 110 is governed by a gantry motor controller 130 that controls the rotational speed and position of the gantry 110. An x-ray source controller 132 provides power and timing signals to the x-ray source 112. Moreover, a table motor controller 134 is configured to control a motorized table 136 to position the patient 120 in the gantry 110. Particularly, the table 136 moves at least a portion of the patient 120 through an opening defined in the gantry 110. The CT imaging system 100 may also include a data acquisition system (DAS) 138 that is configured to sample analog data from detector elements 118 and convert the data analog data to digital data for subsequent processing. The digital data or images reconstructed from the digital data may be stored in a computer, such as for example, the server 18 shown in FIG. 1.

The CT imaging system 100 also includes a plurality of user interfaces 150, such as the user interfaces 16 shown in FIGS. 1-3. In operation, the user interfaces 150 are configured to receive commands from an operator to control the various portions of the CT imaging system 100 via the communication network 14 as well as receive data from the CT imaging system 100. For example, in the illustrated embodiment, the CT imaging system 100 includes a user interface 152 to control the operation of the table 136 via the table motor controller 134. The CT imaging system 100 also includes a user interface 154 to control the operation of the x-ray source 112 via the x-ray source controller 132. The CT imaging system 100 further includes a user interface 156 to control the operation of the gantry 110 via the gantry motor controller 130. Moreover, the CT imaging system 100 additionally includes a user interface 158 to control the operation of the DAS 138. In various other embodiments, the CT imaging system 100 does not include the table motor controller 134, the x-ray source controller 132 or the gantry motor controller 130. Rather, the user interfaces 152, 154, and 156 directly control the operation of the table 136, the x-ray source 112, and the gantry 110, respectively. Moreover, information output from the detector elements 118 may be directly communicated to the user interface 158 to perform various imaging processing procedures. Accordingly, in various embodiments, at least one of the user interfaces 150, e.g. the user interface 158, may include analog-to-digital (A/D) processing circuitry to convert analog signals to digital signals for further processing.

In various embodiments, the user interfaces 16 include applications or widgets to control various controllable devices, components, or modules associated with the CT imaging system 100. For example, the user interface 152 includes a table motor controller application 160 that is programmed to allow control of the operation of the table 136, via the table motor controller 134. Optionally, the user interface 152 may directly control the operation of the table 136 without the use of the table motor controller 134. The user interface 154 includes an x-ray controller application 162 that is programmed to allow control of the operation of the x-ray source 112, via the x-ray source controller 132. Optionally, the user interface 154 may directly control the operation of the x-ray source 112 without the use of the x-ray source controller 132. The user interface 154 includes a gantry motor controller application 164 that is programmed to allow control of the operation of the gantry 110, via the gantry motor controller 130. Optionally, the user interface 156 may directly control the operation of the gantry 110 without the use of the gantry motor controller 130. The user interface 158 includes a DAS controller application 166 that is programmed to control the operation of the DAS 138.

In various embodiments, the server 18 includes a plurality of applications 170 that define a set of controllable operators or functions of the CT imaging system 100. More specifically, in various embodiments, the server 18 includes all of the applications utilized to control and monitor the CT imaging system 100. Thus, the server 18, in various embodiments, includes the table motor controller application 160, the x-ray controller application 162, the gantry motor controller application 164, and the DAS controller application 166. Additionally, the server 18 may also include various other applications or widgets that may be desired by medical personnel as described in more detail below.

Figure 5:
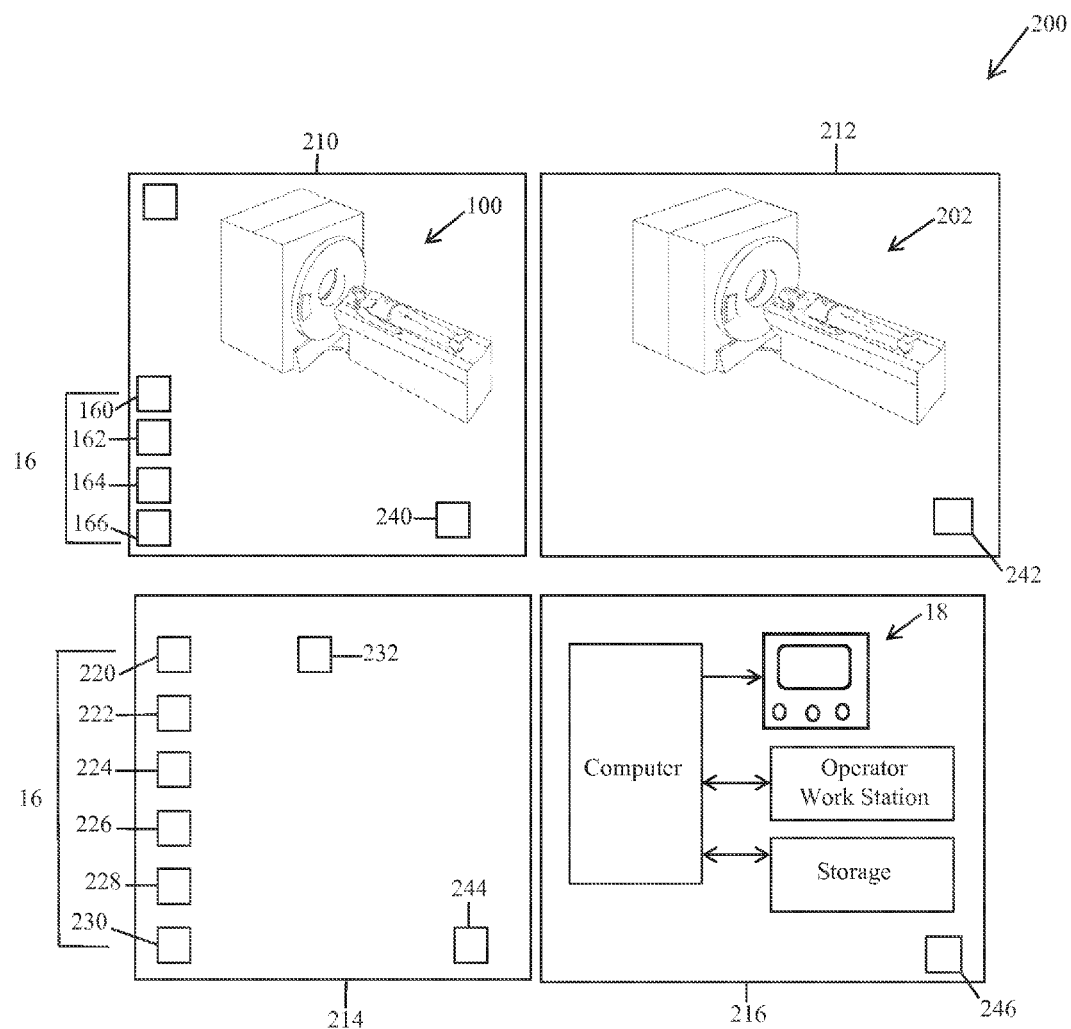
FIG. 5 is a simplified block diagram of an exemplary healthcare facility that may include the control and monitoring system shown in FIG. 1.

FIG. 5 is simplified block diagram of an exemplary healthcare facility 200 that may include the control and monitoring system 10 shown in FIG. 1. Moreover, the healthcare facility 200 may also include the CT imaging system 100 and a second imaging system 202. In the illustrated embodiment, the CT imaging system 100 is installed in a first procedure room 210 and the second imaging system 202 is installed in a second procedure room 212. The healthcare facility 200 may also include a waiting room 214 and a control room 216. In various embodiments, the server 18 may be installed in the control room 216. It should again be realized that although the illustrated embodiments are described in a healthcare setting, the various embodiments described herein may be utilized to control the operation and monitoring of any system and that the healthcare imaging systems described herein are exemplary only. It should also be realized that each of the rooms illustrated in FIG. 5 may also include a communication network similar to the communication network 14 shown in FIG. 1.

As described above, the control and monitoring system 10 includes a plurality of user interfaces 16. In various embodiments, the user interfaces 16 may be temporarily located at various locations within the healthcare facility 200 to enhance the workflow procedures utilized by the medical personnel to perform patient imaging and diagnostic procedures. For example, the user interface 152, the user interface 154, the user interface 156, and the user interface 158 may be located in the first procedure room 210 with the CT imaging system 100 to control and monitor the operation of the table 136, the x-ray source 112, the gantry 110, and the DAS 138, respectively, as described above.

Moreover, the system 10 may also include various other user interfaces 16 for performing various selected healthcare functions. For example, the system 10 may include a user interface 220 for performing patient vital signs applications. More specifically, the user interface 220 may be configured to receive and display patient vital sign information to an operator before assignment of the patient to a physician. The user interface 220 may be hand carried by a nurse, for example, to enable the nurse to input the patient's vital sign information before assignment of the patient to the physician. A user interface 222 may include an application to display a list of patients awaiting a scan using the CT imaging system 100 and/or the imaging system 202. In various embodiments, the user interface 222 may be temporarily located in the waiting room 214 to inform prospective patients of a corresponding appointment time. Moreover, the user interface 222, which may include a display, a user input, wireless connectivity, etc., may be relatively large and configured to enable the user to watch television and/or to display the list of patients in a waiting room.

A user interface 224 may include an application that is configured to receive and display patient information and patient records. In various embodiments, the user interface 224 may be hand carried by a physician into and out of the room 200.

A user interface 226 may include an application to input and display patient billing information which may then be transmitted directly to an insurance company or other medical personnel. A user interface 228 may include an application to assist a radiologist in planning a scan protocol to be implemented by the CT imaging system 100 or the imaging system 202. The user interface 228 may be physically attached, e.g. removably coupled, to an imaging system, such as the CT imaging system 100. Optionally, the user interface 228 may be operated as a mobile device that is hand carried by the physician from the control room 216 to the first room 210, for example. A user interface 230 may include an application for reconstructing and reviewing images based on information received from the CT imaging system 100. The user interface 230 also enables the physician to review the images and dictate or write a diagnosis or healthcare recommendation. A user interface 232 may include an application that enables a user to access a database of patient records and display the various patient records.

In operation, the server 18 functions as a storage repository for storing applications that may be desired by a user to control and monitor the CT imaging system 100 or any of the other various applications described herein. Moreover, it should be realized that the various applications stored in the server 18 may be downloaded to the various user interfaces 16 based on inputs received from the user interfaces 16 as is explained in more detail below. Moreover, it should be realized that additional applications may be uploaded to the server 18 and then downloaded to the various user interfaces 16 based on an input received from the user interface.

In various embodiments, the user interfaces 16 include a firewall or other security program that enables, as well as prohibits, various users from uploading or downloading information to the user interfaces 16. For example, it may be desirable to enable a nurse operating the user interface 220 to download an application to display a list of patients awaiting a scan using the CT imaging system 100. However, it may be desired that the nurse is prohibited from downloading an application for planning a scan protocol into the same user interface 220. Accordingly, the firewall may be set to distinguish applications that may be accessed by various users of the user interfaces. Thus, at least two different levels of access may be provided. In various embodiments, the server computer 18 may also include a firewall to prevent unauthorized access to the server 18 and enforce any limitations on authorized access.

In various embodiments, the user interfaces 16 and/or the server 18 may include various biometric scanning devices to verify the identity of the user attempting to upload or download various applications or other information to and/or from the user interfaces 16 and the server 18. The various biometric scanning devices may include for example, fingerprint scanners, iris scanners, voice recognition devices, etc. In various other embodiments, the user may be identified using, for example, a bar code reader configured to read the user's badge information, a cell phone ID, a personal identification number (PIN), etc. In operation, the user is authenticated by the system 10 to enable the user to utilize specific applications that are based on the user's level of access as determined by the user's identification. Additionally, each of the user interfaces 16 is also authenticated to enable each user interface 16 to communicate over the communication network 14. For example, a user interface that is not authorized to connect to the system 10, such as a mobile phone carried by a patient, may be blocked from uploading, downloading, or communicating with the various devices forming the system 10. Moreover, the system 10 may prohibit unauthorized users from logging onto the Wi-Fi network 14 and controlling the operation of various devices forming a part of the control and monitoring system 10.

The operation of the control and monitoring system 10 is now described with respect to the user interface 152 shown in FIG. 4. However, it should be realized that each of the user interfaces 16 may be configured to operate similarly to the user interface 152 and therefore the operation of the user interface 152 is exemplary only. As described above, the user interface 152 includes a GPS application to enable the user interface 152 to determine a location thereof. Additionally, at least some of the rooms shown in FIG. 5, such as the room 210 includes a communication network such as for example, the communication network 14 shown in FIG. 1. Accordingly, in various embodiments, the user interface 152 is configured to identify whether the user interface 152 is located within the room 210, the room 212, the room 214, or the room 216. Additionally, each of the other user interfaces 16 is also aware of the location, utilizing for example the GPS installed on the user interface 152. Thus, each user interface 16 fanning the control and monitoring system 10 is aware of its own location and the location of the other user interfaces 16 by querying the other user interfaces 16.

More specifically, in operation, each of the user interfaces 16 are communicatively coupled to the network 14 and configured for automatic self-synchronization based on a status of at least one of the controllable devices, e.g. the CT imaging system 100, or a status of at least one of the user interfaces 16. For example, each user interface 16 is configured to automatically identify and locate other user interfaces 16 that are currently coupled via the communication network 14. Thus, in various embodiments, if one of the user interfaces, such as the user interface 152 becomes inoperative and is unable to communicate with the communication network 14, the remaining user interfaces 16 are automatically notified that the user interface device 150 is not functioning or has been physically moved outside the communication network 14. Thus, each of the user interfaces 16, in real time scans the communication network 14 to identify other user interface devices 16 communicating over the communication network 14 in real time. Moreover, each of the user interfaces 16 is also configured to automatically identify various controllable devices communicating on the communication network 14.

Additionally, the server 18 includes the plurality of applications 170 for controlling and monitoring the imaging system 10. The server 18 may also include various other applications described above. In various embodiments, the set of applications 170 may be divided into at least two groups of applications. A first group of applications, referred to herein as local control applications, are configured to be utilized within a designated area, such as the room 210 or within a predetermined distance of the system or the controllable device desired to be controlled, e.g. within a predetermined distance of, for example, the CT imaging system 100. A second group of applications, referred to herein as, roving applications, or non-local applications, are configured to be utilized within the predetermined distance or remotely from the system being controlled. For example, in various embodiments, the table motor controller application 160 may be designated as a local control application, such that the user interface 16 attempting to utilize the table motor controller application 160 must be within a predetermined distance of the CT imaging system 100 to operate the table 136. Applications are generally designated as local control applications when it is desired that the user operating the application be able to visually observe the system, or the portion of the system, being controlled. Whereas, other applications designated as the roving applications may be operated near the CT imaging system 100, e.g. inside the room 210, or remotely from the CT imaging system 100, e.g. outside the room 210. For example, in various embodiments, the patient billing and patient scheduling applications may be designated as roving applications and thus may be utilized either in the room 210 having the CT imaging system or in the other rooms 212, 214, and/or 216.

In the illustrated embodiment, the user interface 152 initially includes the application 160, for controlling the operation of the table 136 and is also initially located in the room 210 proximate to the CT imaging system 100. To determine its own location, the user interface 152, in one embodiment, substantially monitors various communication networks. In the illustrated embodiment, the control and monitoring system includes four separate networks 240, 242, 244, and 246, wherein a single network hub is based in each of the rooms 210, 212, 214, and 216, respectively. It should be realized that the system 10 may include more or fewer networks than the networks illustrated in FIG. 5.

Accordingly, the user interface 152 is configured to identify various available networks and determine the proximity of the user interface 152 to any one communication networks based on the signal received by the user interface 152. For example, the user interface 152 may receive a signal from each of the networks 240-244. Moreover, it should be appreciated that the nearer the user interface 152 is to a communication network, the stronger the signal that is received from the communication network. Thus, when the signal received by the user interface 152 is greater than a predetermined level or has the largest power level compared to signals received from other communication networks, e.g. the networks 242, 244, and 246, the user interface 152 determines that it is located within the room 210 which includes the communication network 240 and all applications designated as local control applications on the user interface 152 are operational. In the exemplary embodiment, each of the user interfaces 16 is therefore aware of its own location and configured to automatically activate an appropriate application to provide the needed services for that location. For example, in the illustrated embodiment, the user interface 152 is designated to be located in the room 210. Thus, once the user interface 152 determines that it is in the room 210, the user interface 152 automatically activates the table motor controller application 160 which is also designated as a local control application for the room 210, and is therefore configured to control and/or operate the table 136. In various other embodiments, when the user interface 154 is located on the CT imaging system 100, the user interface 154 automatically activates the x-ray controller application. Similarly, for example, if the user interface 222 determines that it is located in the waiting room 214, which is this embodiment is its designated location, the user interface 222 may automatically activate the application to display the list of patients awaiting a scan using the CT imaging system 100 and/or the imaging system 202.

In various embodiments, the user interface 152 may become inoperative. In this case, because the various user interfaces 16 are automatically self-synchronizing with the other user interfaces 16, the other user interfaces 16 are aware that the user interface 152 is inoperative. In this case, one of the user interfaces 16 located in the room 210 automatically assumes a dual function—its original function and the functions of the user interface 152. For example, the user interface 154, or various other user interfaces 16, may include the table motor controller application 160. However, if the primary user interface for operating the table motor controller application, e.g. the user interface 152 is operational, the user interface 152 operates the table motor controller. However, once the user interface 152 becomes inoperable, the table motor controller application 160 may be implemented by, for example, the user interface 154 which also includes the x-ray controller application 162. Accordingly, in the illustrated embodiment, the user interface 154 may automatically download the table motor controller application 160 from the server 18 to enable the user interface 154 to operate both the table motor controller application 160 and the x-ray controller application 162. It should be realized that any of the user interfaces 16 may be configured to perform the functions of the user interface 152 once the user interface 152 becomes inoperative.

Similarly, as described above, each of the user interfaces 16 is aware of its location. Moreover, some of the applications, such as the table motor controller application 160, may be designated as local control applications. Thus, if the user interface 152 is removed from the room 210, the table motor controller application 160 becomes inoperative as being outside the room 210, e.g. outside its designated area. In this case, the table motor controller application 160 may again be implemented by, for example the user interface 154, which also includes the x-ray controller application 162. Accordingly, in the illustrated embodiment, the user interface 154 may automatically download the table motor controller application 160 from the server 18 to enable the user interface 154 to operate both the table motor controller application 160 and the x-ray controller application 162. It should be realized that any of the user interfaces 16 may be configured to perform the functions of the user interface 154 once the user interface 154 is removed from the room 210.

In various embodiments, both the user interface 152 and the user interface 154 may become inoperative or be removed from the room 210. Because the various user interfaces 16 are automatically self-synchronizing with the other user interfaces 16, the other user interfaces 16 are aware that the user interfaces 152 and 154 are inoperative. In this case, one of the user interfaces 16 located in the room 210 automatically assumes the functions of the user interfaces 152 and 154. For example, the user interface 156, which includes the gantry motor controller application 164, may also be configured to include the table motor controller application 160 and the x-ray controller application 162. Accordingly, in the illustrated embodiment, the user interface 156 may automatically download the table motor controller application 160 and the x-ray controller application 162 from the server 18 to enable the user interface 156 to operate the table motor controller application 160, the x-ray controller application 162, and the gantry motor controller application 164. In other embodiments, various applications may be preloaded into at least some of the user interfaces 16 and then activated when at least one of the user interfaces becomes inoperative or is removed from the communication network 14. It should be realized that any of the user interfaces 16 may be configured to perform the functions of the user interface 154 once the user interface 154 becomes inoperative.

In various embodiments, the user interface 152, the user interface 154, and the user interface 156 may become inoperative or be removed from the room 210. Because the various user interfaces 16 are automatically self-synchronizing with the other user interfaces 16, the other user interfaces 16 are aware that the user interfaces 152, 154, and 156 are inoperative. In this case, one of the user interfaces 16 located in the room 210 automatically assumes the functions of the user interfaces 152, 154, and 156. For example, the user interface 158, which includes the DAS application 158, may also be configured to include the table motor controller application 160, the x-ray controller application 162, and the gantry motor controller application 164. Accordingly, in the illustrated embodiment, the user interface 158 may automatically download the table motor controller application 160, the x-ray controller application 162, and the gantry motor controller application 164 from the server 18 to enable the user interface 158 to operate the table motor controller application 160, the x-ray controller application 162, the gantry motor controller application 164, and the DAS application 166. It should be realized that any of the user interfaces 16 may be configured to perform the functions of the user interface 156 once the user interface 156 becomes inoperative. Accordingly, when one or more of the user interfaces 16 is removed from the communication network 14 or becomes inoperative, the remaining user interfaces 16 are configured to automatically assume the functions of the inoperative user interface.

Moreover, when a user interface 16 becomes operative or re-enters the room 210, the user interfaces 16 currently located in the room 210 again automatically reconfigure based on the newly identified user interface. For example, assume, as described above, that the user interfaces 152, 154, and 156 are inoperative or removed from the room 210 such that the user interface 158 is performing the applications designated to the user interfaces 152, 154, and 156. Again, assume that the user interface 156 becomes operative or re-enters the room 210. In this case, the user interface 156 automatically assumes control of the gantry 110 using the gantry motor controller application 164. Moreover, the user interface 158 continues to operate the table motor controller application 160, the x-ray controller application 162 and the DAS application 166. Similarly, if the user interface 154 becomes operative or re-enters the room 210, the user interface 154 automatically assumes control of the x-ray source 112 via the x-ray controller application 162. Moreover, the user interface 156 continues to operate the gantry motor controller application 164 and the user interface 158 continues to operate the table motor controller application 160 and the DAS application 166. Finally, if the user interface 152 becomes operative or re-enters the room 210, the user interface 152 automatically assumes control of the table 136 via the table motor controller application 160, the user interface 154 automatically retains control of the x-ray source 112 via the x-ray controller application 162, the user interface 156 continues to operate the gantry motor controller application 164 and the user interface 158 continues to operate the table motor controller application 160 and the DAS application 166.

Accordingly, in various embodiments, the user interfaces 16 are configured to determine when a user interface 16 is removed from the communication network 14 utilizing the GPS system or a loss of communication with the communication network 14. Moreover, when a user interface 16 re-enters the communication network 14, the user interface 16 is configured to present verification credentials to be authorized to re-enter the communication network 14. For example, a user interface may be configured to automatically lock up once the user interface is taken out of its assigned vicinity and automatically re-authenticate once it is brought back into its assigned vicinity. In operation, the user interfaces 16 are therefore able to form a communication network and automatically exchange information once they are authenticated as being part of the communication network. For example, a user interface can know, using the GPS system, when a radiologist returns to the hospital, and uploads reports that the radiologist has prepared from home while downloading new cases automatically.

Figure 6:
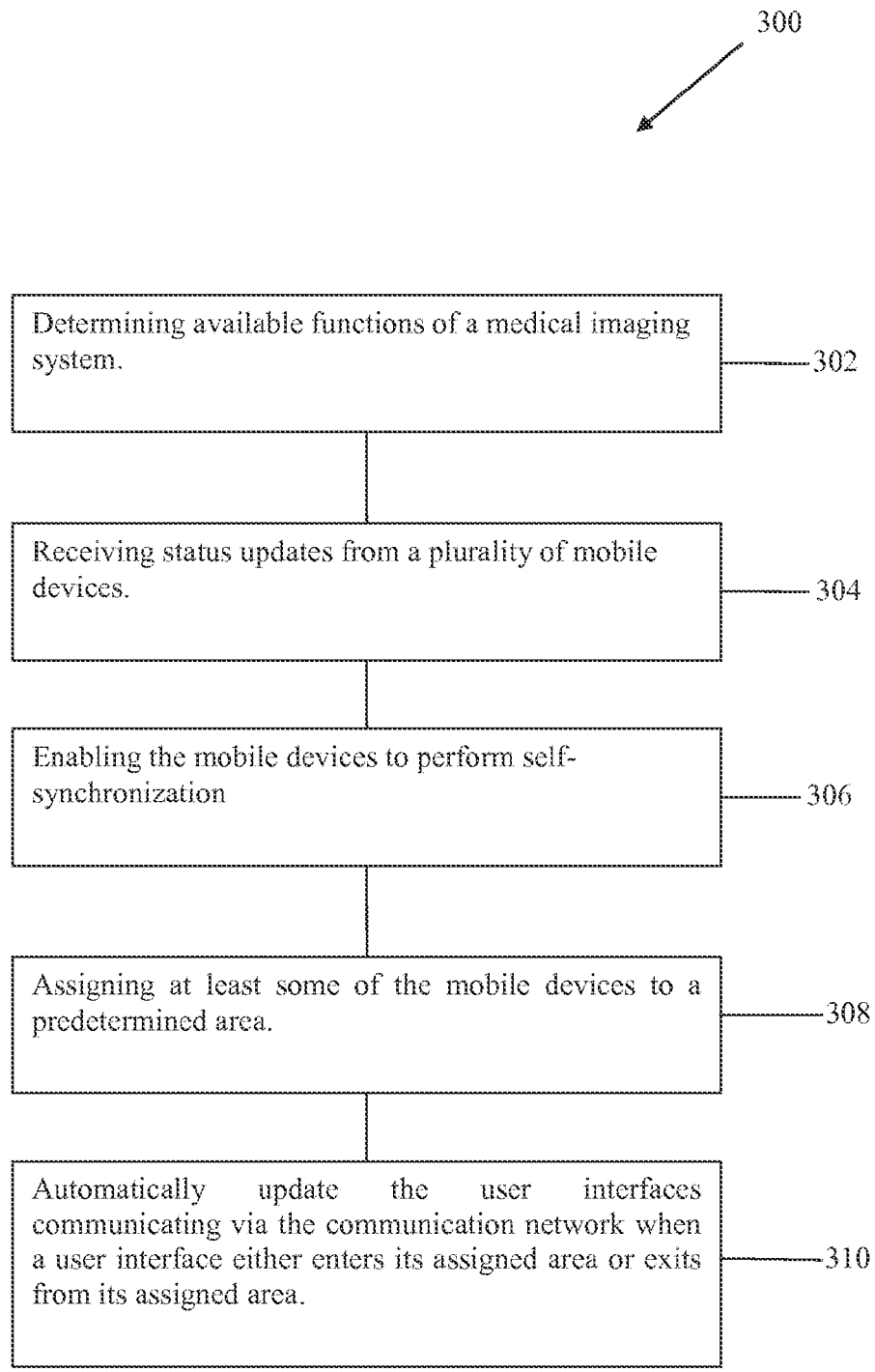
FIG. 6 is a flowchart of an exemplary method of controlling a medical system in accordance with various embodiments.

FIG. 6 is a flowchart of an exemplary method 300 of controlling and/or monitoring a medical system, such as the medical system 12 shown in FIG. 1. At 302, available functions of a medical imaging system are determined. In various embodiments, the available functions may include, for example, the ability to control the table 136, control the x-ray source 112, etc. At 304, status updates are received from a plurality of mobile devices. The mobile devices may be the user interfaces 16, for example. Moreover, the status updates may include the availability of various user devices 16 to perform various functions or to control and/or monitor the system 12. For example, as described above, when a user interface leaves the predetermined area, the user interface may, in some embodiments, no longer be able to control or monitor the system 12. Accordingly, the mobile devices, e.g. the user interfaces 16 receive status updates from the other user interfaces 16 to identify which user interfaces 16 are available in the communication network 14. At 306, the mobile devices are enabled to perform self-synchronization. More specifically, in various embodiments, the user interfaces 16 are configured to automatically self-synchronize with each other to enable information to be shared among the user interfaces 16. At 308, the mobile devices 16 are assigned to a predetermined area as described above. At 310, the user interfaces 16 communicating via the communication network 14 are automatically updated when a user interface 16 either enters its assigned area or exits from its assigned area.

Thus, various embodiments provide a control and monitoring system for controlling one or more medical systems. The control and monitoring system includes a plurality of user interfaces that are implemented as portable touch screen devices. Each of the user interfaces is aware of its own location and the location of other user interfaces coupled to the communication network. In the event that a user interface is removed within a specified distance from its assigned location, the applications installed on the user interface may be configured to self-disable or sound an alarm on the device, on other devices in the grid, or in a central location for security reasons. Optionally, when the user interface is removed from its assigned location, various local control applications on the user interface may become automatically inoperative, but will automatically reconnect to the grid once it is brought back to the vicinity of it assigned location.

Accordingly, each user interface is aware that it is part of a grid of modular user interfaces. Thus, if one user interface becomes inoperative, another user interface can serve its assigned functions which make the system redundant and increases fault tolerance. In various embodiments, a single user interface may operate the system when the other user interfaces are inoperative or removed from the communication network. Accordingly, each user interface is automatically self-reconfigurable after sending appropriate notifications about the missing or faulty user interfaces.

Moreover, the user interfaces may automatically reconfigure based on the preferences of the logged in user. More specifically, when a user logs in and sets some preferences, the preferences are made available to other user interfaces as well. For example, a radiologist who prefers to look at images using a particular contrast does not need to set his preference on each user interface.

In order to control imaging system in real time, the modular control and monitoring system has the capability for synchronization across the highly interconnected grid network. In various embodiments, each user interface has at least two modes of connection, such as for example, Wi-Fi, Ethernet, Bluetooth, infra-red, or a wired connection, etc.

The various embodiments and/or components, for example, the modules, or components and controllers therein, also may be implemented as part of one or more computers or processors. The computer or processor may include a computing device, an input device, a display unit and an interface, for example, for accessing the Internet or local network. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A modular control system comprising:
    a plurality of individual touch screen devices, each touch screen device including a display unit, a touch input, a computing device, a network connection, and a programming logic for controlling a remote medical system and displaying a status of the remote medical system on the touch screen device, wherein at least one of the touch screen devices includes a local control application, the local control application configured to activate when the at least one touch screen device is located within a predetermined area and deactivate when the at least one touch screen device is outside the predetermined area, wherein the predetermined area is based on a location of a remote medical device;
    the remote medical system having network connectivity to enable the remote medical system to exchange information with and respond to instructions from the touch screen devices, the touch screen devices configured for automatic self-synchronization based on a status of the remote medical system or a status of at least one of the touch screen devices.

2. The modular control system of claim 1, wherein at least one of the controllable devices comprises a medical imaging system.

3. The modular control system of claim 1, wherein more than one of the touch screen devices may be configured to control the remote medical system or be controlled by a one of the touch screen devices.

4. The modular control system of claim 1, wherein the communication grid comprises a wireless local network and the user interface is configured to dynamically change its interface based on its location with respect to the system being controlled.

5. The modular control system of claim 1, wherein the plurality of touch screen devices further comprises:
    a first touch screen device assigned to a first area, the first touch screen device having a first local control application installed thereon; and
    a second touch screen device assigned to the first area, the second touch screen device configured to automatically detect when the first touch screen device is outside the first area.

6. The modular control system of claim 1, wherein the plurality of touch screen devices further comprise:
a touch screen device assigned to a first area, the first touch screen device having a local control application installed thereon, the first touch screen device automatically deactivating the local control program when the first touch screen device is not in the first area.

7. The modular control system of claim 1, wherein at least one of the touch screen device is assigned to a predetermined location, the touch screen device further configured to operate only a predetermined set of applications when the touch screen device is within the predetermined area.

8. The modular control system of claim 1, wherein to automatic self-synchronize, each touch screen device is configured to identify a location of other touch screen devices within the control and monitoring system and enable information to be shared among the touch screen devices.

9. The modular control system of claim 1, wherein at least one of the touch screen device is configured to enable an operator to input viewing and operational preferences.

10. A modular control system comprising:
a system configured to communicate with a network; and
a plurality of individual touch screen devices, each touch screen device including a display unit, a touch input, a computing device, a network connection, and a programming logic for controlling a remote medical system and displaying a status of the remote medical system on the touch screen device,
the system having network connectivity to enable the system to exchange information with and respond to instructions from the touch screen devices, the touch screen devices configured for automatic self-synchronization based on a status of the remote medical system or a status of at least one of the touch screen devices, wherein each of the plurality of touch screen devices is configured to communicate with the other touch screen devices in the system and adjust a function installed on at least one of the touch screen devices based on feedback from other touch screen devices.

11. The modular control system of claim 10, wherein at least some of the portable touch screen devices are configured to authenticate a user operating the portable touch screen device using at least one of face recognition, a finger print, a predefined password, a predefined gesture, a pre-assigned identification badge, or voice recognition.

12. The modular control system of claim 10, wherein each of the portable touch screen devices is location aware, and is configured to automatically adjust functions and dynamically reconfigure a graphical user interface based on a location of the portable touch screen device.

13. The modular control system of claim 10, wherein the system comprises a medical imaging system.

14. The modular control system of claim 10, wherein at least one of the touch screen devices includes at least one local control program, the at least one touch screen device activating the local control program when the touch screen device is within a predetermined distance of the system and deactivating the local control program when the touch screen device is not within the predetermined distance of the system;
wherein to automatic self-synchronize, each touch screen device is configured to identify a location of other touch screen devices within the control and monitoring system and enable information to be shared among the touch screen devices.

* * * * *